US012806442B2

(12) United States Patent
Ma et al.

(10) Patent No.: US 12,806,442 B2
(45) Date of Patent: Nov. 24, 2026

(54) METHOD AND SYSTEM FOR DETERMINING A TEMPOROSPATIALLY-FRACTIONATED RADIOTHERAPY PLANNING

(71) Applicant: CANCER HOSPITAL, CHINESE ACADEMY OF MEDICAL SCIENCES AND PEKING UNION MEDICAL COLLEGE, Beijing (CN)

(72) Inventors: Min Ma, Beijing (CN); Jianrong Dai, Beijing (CN)

(73) Assignee: CANCER HOSPITAL, CHINESE ACADEMY OF MEDICAL SCIENCES AND PEKING UNION MEDICAL COLLEGE, Beijing (CN)

( * ) Notice: Subject to any disclaimer, the term of this patent is extended or adjusted under 35 U.S.C. 154(b) by 403 days.

(21) Appl. No.: 18/739,377

(22) Filed: Jun. 11, 2024

(65) Prior Publication Data

US 2024/0424320 A1 Dec. 26, 2024

(30) Foreign Application Priority Data

Jun. 14, 2023 (CN) ......................... 202310705978.7

(51) Int. Cl.
*A61N 5/00* (2006.01)
*A61N 5/10* (2006.01)

(52) U.S. Cl.
CPC ......... *A61N 5/1031* (2013.01); *A61N 5/1039* (2013.01)

(58) Field of Classification Search
CPC .... A61N 5/1031; A61N 5/1039; A61N 5/103; G16H 20/40; G16H 30/00; G16H 50/50; Y02T 10/40
See application file for complete search history.

(56) References Cited

U.S. PATENT DOCUMENTS

2019/0336795 A1* 11/2019 Zhou ........................ A61B 6/03

* cited by examiner

*Primary Examiner* — Dani Fox
(74) *Attorney, Agent, or Firm* — CBM PATENT CONSULTING, LLC

(57) ABSTRACT

A method and system for determining a spatiotemporal fractionation radiotherapy planning, belonging to the technical field of medical equipment which involves acquiring pathological images; identifying the acquired pathological images to determine the region of interest in the pathological images as the radiotherapy region; arranging the irradiation field direction according to the shape of the radiotherapy region, setting the optimization conditions of the radiotherapy planning according to clinical prescription requirements, and planning the radiotherapy path; evaluating the plan quality based on the planned optimization model for the planned radiotherapy path, and resetting the optimization conditions for unsuitable radiotherapy plans until the plan quality meets the requirements; outputting the radiotherapy path that meets the plan quality requirements as the final spatiotemporal fractionation radiotherapy plan.

8 Claims, 3 Drawing Sheets

METHOD AND SYSTEM FOR DETERMINING A TEMPOROSPATIALLY-FRACTIONATED RADIOTHERAPY PLANNING

CROSS-REFERENCE TO RELATED APPLICATIONS

This application claims priority to Chinese Patent Application Ser. No. CN2023107059787 filed on 14 Jun. 2023.

TECHNICAL FIELD

The invention relates to the technical field of medical equipment, specifically to a method and system for determining a TemporoSpatially-Fractionated Radiotherapy planning.

BACKGROUND TECHNOLOGY

Currently, radiotherapy technologies that combine physical technology and biological mechanisms mainly include ultra-high dose rate radiotherapy and spatially fractionation radiotherapy.

Ultra-high dose rate radiotherapy (also known as FLASH radiotherapy) refers to radiotherapy performed at a dose rate of 40 Gy/s, which has an equivalent tumor treatment response to conventional irradiation while providing significant protective effects on normal tissues.

Ultra-high dose rate radiotherapy, due to its extremely short radiation delivery time, changes the biological effects on normal tissues compared to traditional radiotherapy. It also addresses the issue of organ motion management in current clinical treatments, enhancing patient comfort and treatment efficiency.

Spatially fractionated radiotherapy refers to dividing the originally uniform target dose distribution into uneven dose distributions, with high-dose areas called peaks and low-dose areas called valleys. The peak-valley effect in spatially fractionated radiotherapy benefits the repair of normal tissues and significantly enhances the radiobiological effects on tumors. Spatially fractionated radiotherapy is a type of large fraction radiotherapy, which markedly improves the radiobiological effects on tumors.

Spatially fractionated radiotherapy techniques include Grid radiotherapy, Lattice radiotherapy, Minibeam (MRT) radiotherapy, and Microbeam (MBRT) radiotherapy. Currently, Grid and Lattice are in clinical use, while Minibeam and Microbeam are still in the research stage. The main differences among these four techniques lie in the size of the beamlet and the spacing between them. The beamlet size for Grid and Lattice radiotherapy is on the centimeter scale, minibeam radiotherapy reduces the beamlet size to millimeters to several hundred micrometers, and microbeam radiotherapy further reduces the beamlet size to tens of micrometers. The spacing between beamlets is generally comparable to or several times the size of the beamlets.

Spatially fractionated radiotherapy has advantages in palliative treatment for large tumors in the middle and late stages, with an objective response rate as high as 80-90%; if combined with conventional external irradiation, the objective response rate can be further increased to 92%. Specific applications include advanced large primary head and neck tumors, lung tumors, cervical cancer, and sarcomas. With the continuous advancement of spatially fractionated radiotherapy technology and clinical application research, it may be possible to apply it to the treatment of patients with earlier stages of tumors in the future.

Although ultra-high dose rate radiotherapy has a research history of 60-70 years, its radiobiological effect mechanism is still being explored, and clinical trials of ultra-high dose rate radiotherapy are still in the early stages. This indicates that ultra-high dose rate radiotherapy is still quite far from routine clinical application. Despite some clinical applications of spatially fractionated radiotherapy achieving good efficacy, there are still issues: the radiobiological mechanism has not been fully elucidated; there is no theoretical basis for the values of beamlet size and spacing, and the actual application varies greatly among different institution; there is no dedicated spatially fractionated radiotherapy planning system, requiring manual arrangement of the spatially fractionated radiotherapy target area. Radiotherapy physical technology is constantly innovating, but the cost of new technology is rising rapidly, while the improvement in patient efficacy is slow, ultimately leading to a rapid decline in the cost-effectiveness of new technology. Given this situation, colleagues at home and abroad have begun to shift more attention to the research combining physical technology and biological mechanisms, hoping to achieve major breakthroughs and promote the further development of radiotherapy.

Current research indicates that spatially fractionated radiotherapy does not show dependence on oxygen concentration, but ultra-high dose rate radiotherapy does exhibit such dependence. Additionally, the very short treatment time of ultra-high dose rate radiotherapy is beneficial for treating moving organs, reducing the requirements for organ motion management. In contrast, spatially fractionated radiotherapy, when using very small and closely spaced beamlet, such as MRT, may cause beam path blurring due to organ motion (heart and respiratory motion) during treatment. Clearly, combining these two research hotspots can complement each other's shortcomings. Judith Reindl et al. reviewed the combination of ultra-high dose rate radiotherapy and proton microbeam, indicating that proton microbeam radiotherapy alone or in combination with ultra-high dose rate radiotherapy is a promising method for future tumor treatment. Bertho et al. first evaluated the effects of combining temporal and spatial fractionation with proton minibeam radiotherapy on glioma-bearing rats. When the dose was administered in two fractions, the number of long-term survivors was 2.2 times higher than with a single fraction. Compared to standard radiotherapy, the damage to normal tissue remained minimal and was reduced. Wright et al. studied the effects of ultra-high dose rate microbeam radiotherapy on normal lung tissue in rats. They found that ultra-high dose rate microbeam radiotherapy increased the radiation tolerance of normal tissue by an order of magnitude. Therefore, ultra-high dose rate microbeam radiotherapy reduces damage to normal tissue and can improve radiotherapy efficacy by increasing the dose.

SUMMARY OF THE INVENTION

The purpose of the invention is to provide a method and system for determining a temporospatially-fractionated radiotherapy planning, to solve at least one of the technical problems existing in the background technology described above.

To achieve the above purpose, the invention adopts the following technical solutions:

On one hand, the present invention provides a method for determining a temporospatially-fractionated radiotherapy planning, which includes:

Obtaining pathological images;

Identifying the obtained pathological images to determine the region of interest in the pathological images as the radiotherapy region;

Arranging the irradiation field direction according to the shape of the radiotherapy region, setting the optimization conditions of the radiotherapy planning according to clinical prescription requirements, and planning the radiotherapy path;

For the planned radiotherapy path, evaluate the plan quality based on the plan optimization model, and reset the optimization conditions for unsuitable radiotherapy plans until the plan quality meets the requirements;

Output the radiotherapy path that meets the plan quality requirements as the final spatiotemporal fractionation radiotherapy plan.

Optionally, the establishment of the plan optimization model includes: establishing a dose modification factor model using the dose modification factor method; integrating the established dose modification factor model into the standard linear-quadratic model to construct a new linear-quadratic model; based on the linear-quadratic model, combining the expected clinical goals of clinical target area coverage and organ-at-risk protection to construct the plan optimization model.

Optionally, using the dose modification factor method, combined with the temporally fractionated effect, spatially fractionated effect, and the synergistic effect between the temporally and spatially fractionated effects, define the dose modification factor model, expressed by the formula:

$$M = M^T \times M^S \times M^{TSS};$$

where M represents the total dose modification factor; $M^T$ represents the biological effect of temporally fractionated radiotherapy; $M^S$ represents the biological effect of spatially fractionated radiotherapy; $M^{TSS}$ represents the synergistic effect between temporally and spatially fractionated effects.

Optionally, constructing a linear-quadratic model includes:

If the doses of all fractionated irradiations in a course are the same, the total biological effective dose for the course is:

$$B_i = nD_i\left(1 + \frac{D_i}{(\alpha/\beta)_i}\right)$$

where $B_i$ is the biological effective dose for voxel i, n is the number of irradiations, $D_i$ is the fractionated physical dose, and $(\alpha/\beta)_i$ is the biological characteristic dose of the tissue.

Integrate the dose modification factor model M into the standard LQ model to obtain a new expression of the LQ model:

$$B_i = \sum_{k=1}^{n}\left[M_{ki}D_{ki} + \frac{1}{(\alpha/\beta)_i}(M_{ki}D_{ki})^2\right]$$

Where, $M_{ki}$ represents the dose modification factor for the biological effect at the kth fraction for voxel i.

Optionally, considering the expected clinical goals of clinical target coverage and organ-at-risk protection, the plan optimization model is as follows:

The objective function is:

$$\text{Minimize } f(B) = w_{T,1}\sum_{i\in T}(B_T^{min} - B_i)_+^2 + w_{T,2}\sum_{i\in T}(B_i - B_T^{min})_+^2 + w_{O,1}\sum_{i\in O}(B_i - B_i^{max})_+^2 + w_{O,2}\sum_{i\in O}(B_i - B_i^{mean})_+^2 + w_{O,3}\sum_{i\in O}B_i - W_{T,3}\sum_{i\in T}B_i$$

The constraints are:

$$B_i \le B_O^{max}\ \forall\ i\in O$$

$$B_i \le B_T^{max}\ \forall\ i\in T$$

$$B_i = \sum_{k=1}^{n} B_{ki}\ \forall\ i$$

$$B_{ki} = D_{ki} + \frac{1}{(\alpha/\beta)_i}D_{ki}^2\ \forall\ i, \forall\ k$$

$$D_{ki} = \sum_j M_{kij}d_{ij}x_{kj}\ \forall\ i, \forall\ k$$

$$x_{kj} \ge 0\ \forall\ j, \forall\ k$$

Where, the objective function $f(B)$ represents the expected clinical goals of target coverage and organ-at-risk protection; the first term of the objective function represents the positive contribution of the minimum BED value ratio $B_i$ in the low-dose region of the target, the second term represents the positive contribution of the maximum BED value ratio $B_i$ in the high-dose region of the target, the third and fourth terms represent the positive contributions of the maximum and average BED values ratio $B_i$ in the organ-at-risk regions, the fifth and sixth terms represent the average BED value of normal tissue and the average BED value of the target; T represents the set of voxels contained in the target, O represents the set of all organ-at-risk tissue voxels, $w_T$ represents the relative importance weight for the target goal, $w_B$ represents the relative importance weight for the normal tissue goal, $$B_T^{min}$$

represents the minimum BED value of the target, $$B_O^{max}$$

represents the maximum BED value of normal tissue, $$B_i^{mean}$$

represents the average BED value of the respective tissue, $$B_i^{max}$$

represents the maximum BED value of the respective tissue, $D_{ki}$ is the physical dose of the voxel i in the kth fraction, $d_{ij}$ the dose-deposition matrix represents the dose contribution of the beam j per unit flux to the voxel i, $x_{kj}$ represents the flux weight of the beam j in the kth fraction, $B_i$ is the BED value of voxel i, $M_{kij}$ is the dose modification factor of beam j in voxel i in the kth fraction.

Optionally, the calculation formula for the dose modification factor of the ultra-high dose rate effect $M^T$ is as follows:

$$M^T = \begin{cases} C, & \dot{D} \geq 40\ Gy/s \\ 1, & \dot{D} < 40\ Gy/s \end{cases}$$

$\dot{D}$ represents the dose rate, which is greater than or equal to 40 Gy/s considering the ultra-high dose rate effect; less than 40 Gy/s that does not consider the ultra-high dose rate effect, C is a constant related to tissue characteristics.

The calculation formula for the dose modification factor of the spatially fractionated effect $M^S$ is as follows:

$$M^S = \begin{cases} \dfrac{2\beta D_{x\text{-}rays}}{-\alpha + \sqrt{\alpha^2 - 4\beta \ln\left(P_0 + (1 - P_0)e^{-k\tau}\right)}}, & 0 \leq R \leq 20\ \text{mm} \\ 1, & R > 20\ \text{mm} \end{cases}$$

$\alpha$ and $\beta$ are cell-specific parameters, $D_{x\text{-}rays}$ representing the physical absorbed dose corresponding to 10% cell survival fraction in tumor cells irradiated by X-rays, $P_0$ representing the probability of cell survival after responding to the signal, and k is the response coefficient.

In the second aspect, the present invention provides a system for determining a temporospatially-fractionated radiotherapy planning, including:

Acquisition module, used for acquiring pathological images;

Radiotherapy region determination module, used for identifying the acquired pathological images and determining the region of interest in the pathological images as the radiotherapy region;

Radiotherapy path planning module, used for arranging the irradiation field direction according to the shape of the radiotherapy region, setting the optimization conditions of the radiotherapy plan according to clinical prescription requirements, and planning the radiotherapy path;

Radiotherapy evaluation module, used for evaluating the quality of the planned radiotherapy path based on the plan optimization model, and resetting the optimization conditions for unsuitable radiotherapy plans until the plan quality meets the requirements;

Output module, used to output the radiotherapy path that meets the plan quality requirements, as the final temporospatially-fractionated radiotherapy planning.

Optionally, the radiotherapy area determination module includes an image recognition unit and a radiotherapy area selection unit. The image recognition unit is used to identify the acquired pathological images, and the radiotherapy area selection unit is used to determine the region of interest in the pathological images as the radiotherapy area.

In a third aspect, the invention provides a non-transitory computer-readable storage medium, which is used to store computer instructions. When executed by a processor, the computer instructions implement the method for determining a temporospatially-fractionated radiotherapy planning as described above.

Fourth aspect, the invention provides a computer program product, including a computer program, wherein the computer program, when executed on one or more processors, is used to implement the method for determining a temporospatially-fractionated radiotherapy planning as described above.

Fifth aspect, the invention provides an electronic device, including: a processor, a memory, and a computer program; wherein the processor is connected to the memory, the computer program is stored in the memory, and when the electronic device is running, the processor executes the computer program stored in the memory to cause the electronic device to execute instructions for implementing the method for determining a temporospatially-fractionated radiotherapy planning as described above.

Beneficial effects of the invention: the temporospatially-fractionated method not only includes ultra-high dose rate radiotherapy and spatially fractionated radiotherapy, but also includes areas in the temporospatial domain map that have never been explored; the provided technical conditions can simulate not only the conditions for treating patients in today's clinical practice, such as multiple irradiation directions, field intensity adjustments, and precise positioning, but also conditions that may be used in future clinical treatments, such as (ultra) high dose rates, small beams/microbeams, and temporospatial synchronous fractionation.

The advantages of additional aspects of the present invention will become more apparent in the following description or will be learned through the practice of the invention.

BRIEF DESCRIPTION OF THE DRAWINGS

To illustrate the technical solutions of the embodiments of the invention more clearly, the drawings required for the description of the embodiments will be briefly introduced below. It is evident that the drawings described below are merely some embodiments of the present invention. For those skilled in the art, other drawings can also be obtained based on these drawings without creative efforts.

DETAILED IMPLEMENTATION

Figure 1:
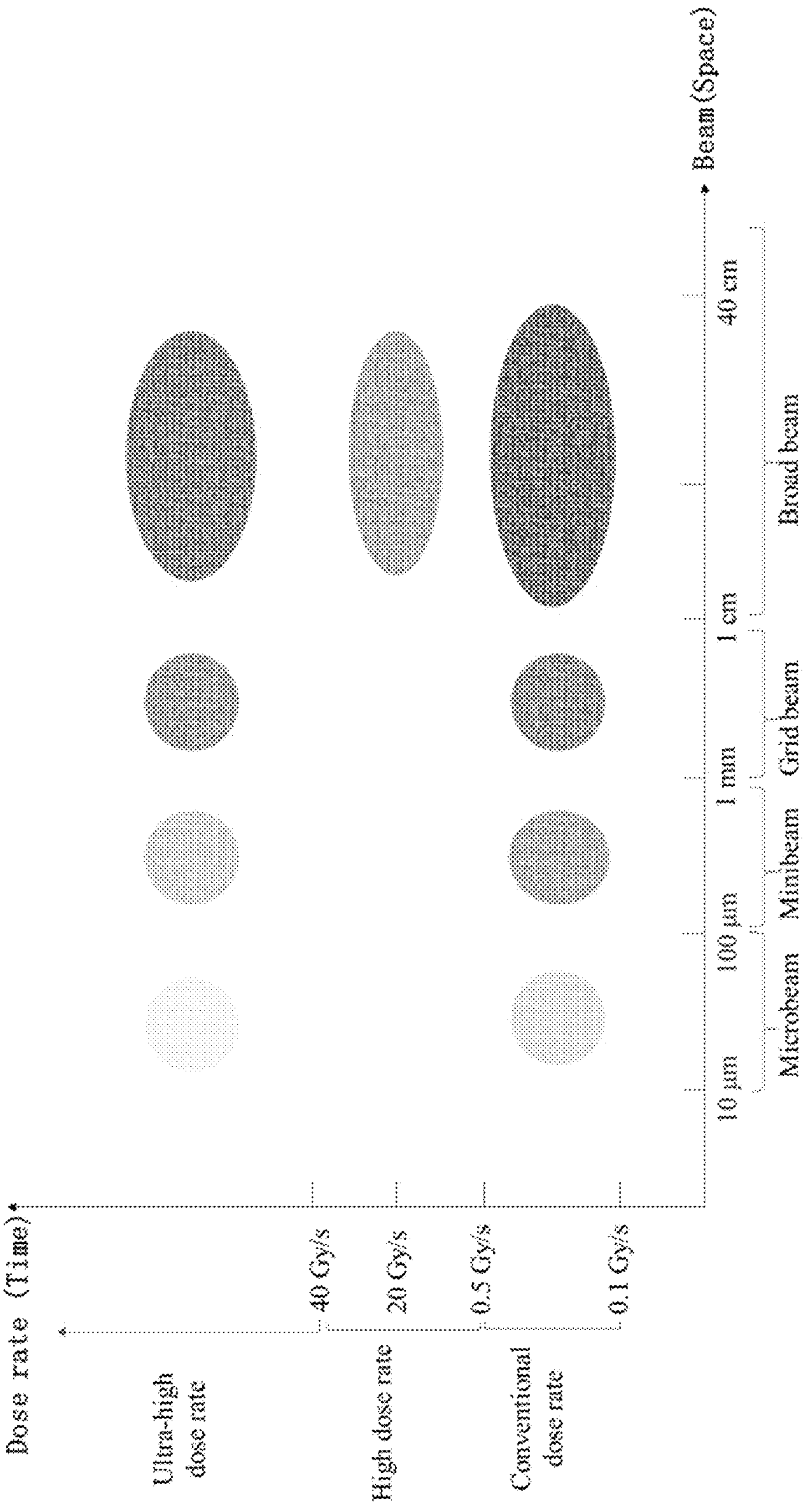
FIG. 1 is a temporospatial domain diagram according to an embodiment of the invention.

The following describes the embodiments of the present invention in detail. The examples of the embodiments are shown in the accompanying drawings, where the same or similar reference numbers indicate the same or similar elements or elements having the same or similar functions throughout. The embodiments described below with reference to the accompanying drawings are exemplary and are only used to explain the present invention, and should not be construed as limiting the present invention.

It will be understood by those skilled in the art that, unless otherwise defined, all terms (including technical and scientific terms) used herein have the same meaning as commonly understood by one of ordinary skill in the art to which this invention belongs.

It should also be understood that terms such as those defined in general dictionaries should be interpreted as having meanings consistent with their context in the relevant art, and should not be interpreted in an idealized or overly formal sense unless expressly defined here.

It will be understood by those skilled in the art that, unless expressly stated otherwise, the singular forms ‘a’, ‘an’, ‘the’, and ‘said’ as used herein also include plural forms. It should further be understood that the term ‘comprising’ as used in the specification of the present invention indicates the presence of stated features, integers, steps, operations, elements, and/or components, but does not preclude the presence or addition of one or more other features, integers, steps, operations, elements, and/or groups thereof.

In the description of this specification, references to terms such as ‘one embodiment,’ ‘some embodiments,’ ‘example,’ ‘specific example,’ or ‘some examples’ mean that the specific features, structures, materials, or characteristics described in connection with the embodiment or example are included in at least one embodiment or example of the present invention. Moreover, the specific features, structures, materials, or characteristics described may be combined in suitable ways in any one or more embodiments or examples. Furthermore, without conflicting, those skilled in the art can combine and integrate different embodiments or examples and the features of different embodiments or examples described in this specification.

To facilitate understanding of the present invention, the following provides a further explanation of the invention in conjunction with the accompanying drawings and specific embodiments, which do not constitute a limitation of the embodiments of the present invention.

Those skilled in the art should understand that the drawings are merely schematic representations of the embodiments, and the components in the drawings are not necessarily essential to the implementation of the present invention.

Example 1

In this Example 1, a system for determining a temporospatial fractionated radiotherapy planning is first provided, which includes:

- Acquisition module, used for acquiring pathological images;
- Radiotherapy region determination module, used for identifying the acquired pathological images and determining the region of interest in the pathological images as the radiotherapy region;
- Radiotherapy path planning module, used for arranging the irradiation field direction according to the shape of the radiotherapy region, setting the optimization conditions of the radiotherapy planning according to clinical prescription requirements, and planning the radiotherapy path;
- Radiotherapy evaluation module, used for evaluating the quality of the planned radiotherapy path based on the plan optimization model, and resetting the optimization conditions for unsuitable radiotherapy plans until the plan quality meets the requirements;
- Output module, used to output the radiotherapy path that meets the plan quality requirements, as the final temporospatial fractionated radiotherapy planning.

The radiotherapy region determination module includes an image recognition unit and a radiotherapy region selection unit. The image recognition unit is used to identify the acquired pathological images, and the radiotherapy region selection unit is used to determine the region of interest in the pathological images as the radiotherapy region.

In this embodiment 1, the above system can achieve a method for determining a temporospatial fractionated radiotherapy planning, including: using the acquisition module to obtain pathological images; using the radiotherapy region determination module to identify the acquired pathological images and determine the region of interest in the pathological images as the radiotherapy region; using the radiotherapy path planning module to arrange the irradiation field direction according to the shape of the radiotherapy region, set the radiotherapy plan optimization conditions according to clinical prescription requirements, and plan the radiotherapy path; using the radiotherapy evaluation module to evaluate the plan quality based on the planned optimal model for the planned radiotherapy path, and reset the optimization conditions for unsuitable radiotherapy plans until the plan quality meets the requirements; using the output module to output the radiotherapy path with the plan quality meeting the requirements as the final temporospatial fractionated radiotherapy planning.

The establishment of the optimization model for the plan includes: using the dose modification factor method to establish a dose modification factor model; integrating the established dose modification factor model into the standard linear quadratic model to construct a new linear quadratic model; based on the linear quadratic model, combining the expected clinical goals of clinical target coverage and organ-at-risk protection to construct the plan optimization model.

Using the dose modification factor method, combining the effects of temporally fractionated radiotherapy, spatially fractionated radiotherapy, and the synergistic effects between temporally and spatially fractionated radiotherapy, the dose modification factor model is defined and expressed by the formula:

$$M = M^T \times M^S \times M^{TSS};$$

where M represents the total dose modification factor; effect; $M^T$ represents the biological effect of temporally fractionated radiotherapy; $M^S$ represents the biological effect of spatially fractionated radiotherapy; $M^{TSS}$ represents the synergistic effect between temporally and spatially fractionated radiotherapy.

Constructing a linear-quadratic model includes:

If the doses of all fractionated irradiations in a course are the same, the total biological effective dose for the course is:

$$B_i = nD_i\left(1 + \frac{D_i}{(\alpha/\beta)_i}\right)$$

where $B_i$ is the biological effective dose for voxel i, n is the number of irradiations, $D_i$ is the fractionated physical dose, and $(\alpha/\beta)_i$ is the biological characteristic dose of the tissue.

Integrate the dose modification factor model M into the standard linear-quadratic model to obtain a new expression of the linear-quadratic model:

$$B_i = \sum_{k=1}^{n}\left[M_{ki}D_{ki} + \frac{1}{(\alpha/\beta)_i}(M_{ki}D_{ki})^2\right]$$

Where, $M_{ki}$ represents the dose modification factor for the biological effect at the kth fraction for voxel i.

Optionally, considering the expected clinical goals of clinical target coverage and organ-at-risk protection, the plan optimization model is as follows:

The objective function is:

$$\text{Minimize} f(B) = w_{T,1}\sum_{i\epsilon T}(B_T^{min} - B_i)_+^2 + w_{T,2}\sum_{i\epsilon T}(B_i - B_T^{min})_+^2 + w_{O,1}\sum_{i\epsilon O}(B_i - B_i^{max})_+^2 + w_{O,2}\sum_{i\epsilon O}(B_i - B_i^{mean})_+^2 + w_{O,3}\sum_{i\epsilon O}B_i - W_{T,3}\sum_{i\epsilon T}B_i$$

The constraints are:

$$B_i \le B_O^{max} \ \forall \ i\epsilon O$$

$$B_i \le B_T^{max} \ \forall \ i\epsilon T$$

$$B_i = \sum_{k=1}^{n} B_{ki} \ \forall \ i$$

$$B_{ki} = D_{ki} + \frac{1}{(\alpha/\beta)_i} D_{ki}^2 \ \forall \ i, \forall \ k$$

$$D_{ki} = \sum_j M_{kij} d_{ij} x_{kj} \ \forall \ i, \forall \ k$$

$$x_{kj} \ge 0 \ \forall \ j, \forall \ k$$

Where, the objective function $f(B)$ represents the expected clinical goals of target coverage and organ-at-risk protection; the first term of the objective function represents the positive contribution of the minimum BED value ratio $B_i$ in the low-dose region of the target, the second term represents the positive contribution of the maximum BED value ratio $B_i$ in the high-dose region of the target, the third and fourth terms represent the positive contributions of the maximum and average BED values ratio $B_i$ in the organ-at-risk regions, the fifth and sixth terms represent the average BED value of normal tissue and the average BED value of the target; T represents the set of voxels contained in the target, O represents the set of all organ-at-risk tissue voxels, $w_T$ represents the relative importance weight for the target goal, $w_B$ represents the relative importance weight for the normal tissue goal, $$B_T^{min}$$

represents the minimum BED value of the target, $$B_O^{max}$$

represents the maximum BED value of normal tissue, $$B_i^{mean}$$

represents the average BED value of the respective tissue, $$B_i^{max}$$

represents the maximum BED value of the respective tissue, $D_{ki}$ is the physical dose of the voxel i in the kth fraction, $d_{ij}$ the dose-deposition matrix represents the dose contribution of the beam j per unit flux to the voxel i, $x_{kj}$ represents the flux weight of the beam j in the kth fraction, $B_i$ is the BED value of voxel i, $M_{kij}$ is the dose modification factor of beam j in voxel i in the kth fraction.

Optionally, the calculation formula for the dose modification factor of the ultra-high dose rate effect $M^T$ is as follows:

$$M^T = \begin{cases} C, & \dot{D} \ge 40 \ Gy/s \\ 1, & \dot{D} < 40 \ Gy/s \end{cases}$$

$\dot{D}$ represents the dose rate, which is greater than or equal to 40 Gy/s considering the ultra-high dose rate effect; less than 40 Gy/s that does not consider the ultra-high dose rate effect, C is a constant related to tissue characteristics.

The calculation formula for the dose modification factor of the spatially fractionated effect $M^S$ is as follows:

$$M^S = \begin{cases} \frac{2\beta D_{x\text{-}rays}}{-\alpha + \sqrt{\alpha^2 - 4\beta \ln(P_0 + (1 - P_0)e^{-k\tau})}}, & 0 \le R \le 20 \ \text{mm} \\ 1, & R > 20 \ \text{mm} \end{cases}$$

α and β are cell-specific parameters, $D_{x\text{-}rays}$ representing the physical absorbed dose corresponding to 10% cell survival fraction in tumor cells irradiated by X-rays, $P_0$ representing the probability of cell survival after responding to the signal, and k is the response coefficient.

Example 2

In this Example 2, a temporospatially-fractionated radiotherapy method is provided, addressing the fundamental issues in the application of temporospatially-fractionated radiotherapy, providing comprehensive technical support for the effective implementation of temporospatially-fractionated radiotherapy, and conducting various radiobiological experiments to discover biological mechanisms, promoting the application of temporospatially-fractionated radiotherapy in clinical practice. A unified dose modification factor model, a unified linear-quadratic model, and a unified plan optimization model are designed; a temporospatially-fractionated radiotherapy system is designed.

In this embodiment, the concept of temporospatially-fractionated radiotherapy is proposed as follows:

If we plot a coordinate system with beamlet size (representing space) on the horizontal axis and dose rate (representing time) on the vertical axis (as shown in FIG. 1), various existing radiotherapy methods based on time and/or space fractionation can be represented in the coordinate system. Since this diagram encompasses all possible time and space fractionation scenarios, it is referred to as the temporospatial domain map in this invention. From the diagram, it can be observed that: (1) The maturity of existing methods varies, with the wide beam field at conventional dose rates being the most mature, and the ultra-high dose rate microbeam method being the least mature. The maturity of the other five methods lies between these two; (2) In the temporospatial domain, there are still large unexplored areas, including high dose rate of microbeam, minibeam, and grid radiotherapy.

As shown in FIG. 1. An (elliptical) circle represents a type of radiotherapy method, different colors represent the maturity of existing methods, the darker the color, the more mature it is, and the blank areas represent unresearched areas. Due to the large data span, the coordinate axis intervals are not strictly proportional. Broad beam is the currently commonly used radiation beam irradiation method in clinical practice, which does not spatially fractionate the target area, resulting in a (relatively) uniform dose distribution within the target area, without peaks and (or) valleys.

From the temporospatial domain map, the existing various methods are not isolated; they are all part of the temporospatial domain. To provide a unified description of the temporal domain and to explore the combination of existing methods and new temporospatial regions in the future, we propose the concept of 'TemporoSpatially-Fractionated Radiotherapy' (TSFRT), which is defined as: a method of fractionating the radiotherapy dose in the temporal dimension and (or) spatial dimension to achieve a better, or even optimal, therapeutic ratio. Fractionation can be performed in a forward manner (i.e., manual trial and error) or in a reverse manner (i.e., automatic optimization). According to this definition, the various radiotherapy methods are specific forms of temporospatial fractionated radiotherapy. For example, ultra-high dose rate broad beam radiotherapy only fractionates the dose in the temporal dimension, i.e., using an ultra-high dose rate to fractionate the dose of a single irradiation within approximately 200 ms. Similarly, conventional dose rate microbeam radiotherapy only fractionates the dose in the spatial dimension, i.e., using 100-1000 μm microbeams (peaks) to provide conventional dose rate irradiation separated by non-irradiated regions (valleys). Furthermore, ultra-high dose rate microbeam radiotherapy fractionates the dose in both the temporal and spatial dimensions, i.e., using both ultra-high dose rates and 100-1000 μm microbeams for irradiation.

The temporospatial fractionated method for radiotherapy not only includes current research hotspots (ultra-high dose rate radiotherapy and spatially fractionated radiotherapy), but also includes areas in the temporospatial domain that have never been explored. Since the core of the temporospatially-fractionated radiotherapy method is independent of the type of radiation beam, it is applicable not only to X-ray beams but can also be extended to other types of beams such as protons, electrons, and carbon ions.

This embodiment temporospatially-fractionated radiotherapy method can be applied to various scenarios that require the combination of spatially fractionated radiotherapy and temporally fractionated radiotherapy, as shown in Table 1 below:

TABLE 1

| Different Types of Plans | | | | |
|---|---|---|---|---|
| | Temporally Fractionated | | | |
| Spatially Fractionated | Broad Beam | Grid (1 cm) | Minibeam (500 μm) | Microbeam (50 μm) |
| Conventional Dose Rate (0.1~0.5 Gy/s) | $P_{11}$ | $P_{21}$ | $P_{31}$ | $P_{41}$ |
| High Dose Rate (20 Gy/s) | $P_{12}$ | $P_{22}$ | $P_{32}$ | $P_{42}$ |
| Ultra-High Dose Rate (40 Gy/s) | $P_{13}$ | $P_{23}$ | $P_{33}$ | $P_{43}$ |
| Ultra-High Dose Rate (60 Gy/s) | $P_{14}$ | $P_{24}$ | $P_{34}$ | $P_{44}$ |
| Ultra-High Dose Rate (80 Gy/s) | $P_{15}$ | $P_{25}$ | $P_{35}$ | $P_{45}$ |

Figure 2:
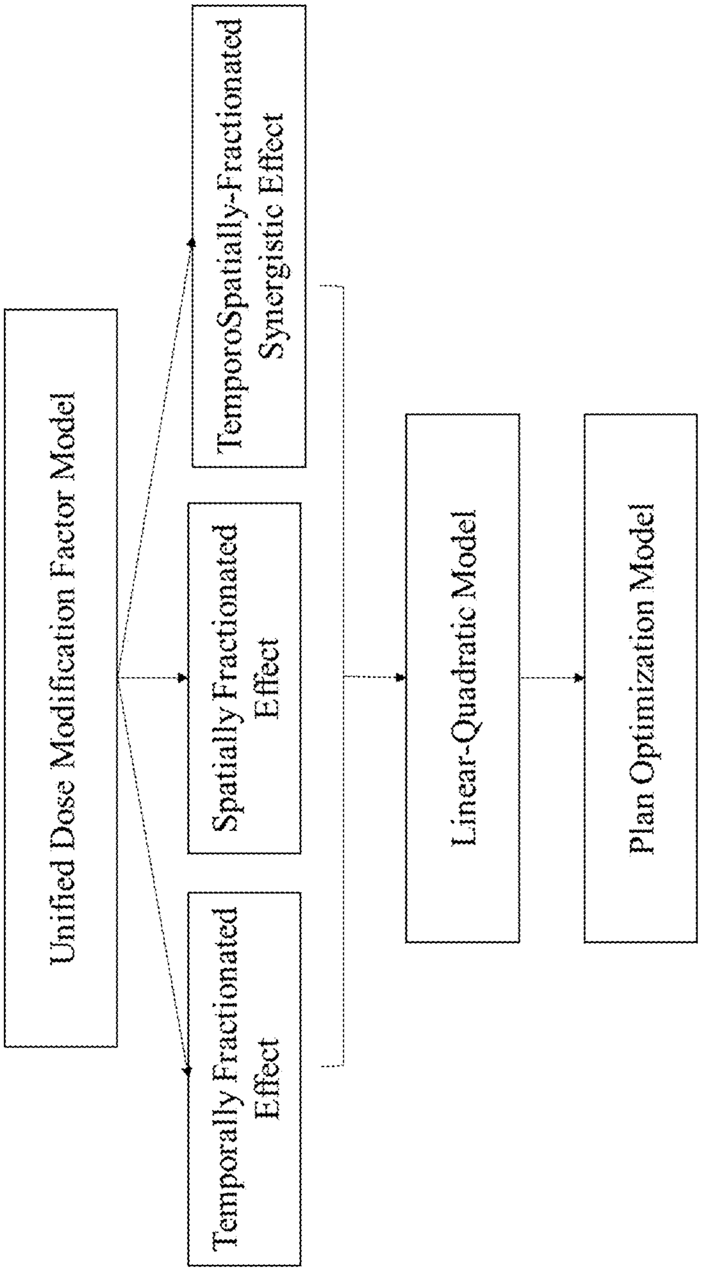
FIG. 2 is a flowchart of the optimal model construction process according to an embodiment of the invention.

In this embodiment, the technical flowchart for constructing the optimal model for the temporospatially-fractionated radiotherapy method is shown in FIG. 2. To ensure that the plan design method can reflect various temporospatially-fractionated radiotherapy methods and their biological effects, this embodiment requires the establishment of a unified dose modification factor model, a Linear-Quadratic Model, and a plan optimization model.

(1) Unified Dose Modification Factor Model

The existing Linear-Quadratic Model does not consider the biological effects caused by temporal fractionation, spatial fractionation, and spatiotemporal synchronous fractionation. For temporally fractionated radiotherapy at ultra-high dose rates, this embodiment uses a dose modifying factor (also known as M) to describe the protective effect of ultra-high dose rates on normal tissues, equating the dose of ultra-high dose rate irradiation to the dose of conventional dose rate irradiation. The dose modifying factor is usually taken as a constant value. For spatially fractionated radiotherapy, a similar approach is used, but the dose modifying factor cannot be a constant and needs to be calculated based on a signal transduction model or other models.

For the temporospatially-fractionated radiotherapy method in this embodiment, the dose modification factor method is also considered. However, since the temporospatially-fractionated radiotherapy method may include three effects: temporally fractionated effect, spatially fractionated effect, and their synergistic effect, we define a unified dose modification factor model, expressed by the formula:

$$M = M^T \times M^S \times M^{TSS}$$

where M represents the total dose modification factor; $M^T$ represents the biological effect of temporally fractionated radiotherapy; $M^S$ represents the biological effect of spatially fractionated radiotherapy; $M^{TSS}$ represents the synergistic effect between temporally and spatially fractionated effects.

(2) Linear-Quadratic Model

The traditional linear-quadratic Model is proposed under the condition of infinite fractions and infinitesimal dose per fraction to produce equal biological effects, but the linear-quadratic model does not consider the biological effects caused by temporal fractionation, spatial fractionation, and spatiotemporal synchronization fractionation. Therefore, it is necessary to find a way to combine these three effects with the linear-quadratic model. This embodiment uses the dose modification factor M to modify the traditional linear-quadratic model and establish a new linear-quadratic model.

According to the traditional linear-quadratic model, if the dose of all fractions in a course of treatment is the same, the total biological effective dose of the course can be expressed as:

$$B_i = nD_i\left(1 + \frac{D_i}{(\alpha/\beta)_i}\right)$$

In the formula, $B_i$ represents the biological effective dose of voxel i, n represents the number of fractions, $D_i$ represents the fractional physical dose, and $(\alpha/\beta)_i$ represents the biological characteristic dose of the tissue. Each tissue has its corresponding biological characteristic dose; the larger the value, the more sensitive the tissue is to radiation, which is reflected in early-responding tissues such as most tumor tissues and epithelial cells. Conversely, the smaller the value, the more resistant the tissue is to radiation, which is reflected in late-responding tissues such as prostate tumors, lungs, and spinal cord.

By integrating the dose modification factor model into the standard linear-quadratic model, the linear-quadratic model can reflect the biological effects caused by temporal fractionation, spatial fractionation, and spatiotemporal synchronous fractionation. Using the dose modification factor M, a new expression of the linear-quadratic model can be obtained:

$$B_i = \sum_{k=1}^{n}\left[M_{ki}D_{ki} + \frac{1}{(\alpha/\beta)_i}(M_{ki}D_{ki})^2\right]$$

Where, $M_{ki}$ represents the dose modification factor for the biological effect at the kth fraction for voxel i.

The temporally fractionated effect, spatially fractionated effect, and temporospatially-fractionated synergistic effect are specific cases of the general form.

(3) Plan Optimization Model

Temporospatially-fractionated radiotherapy involves numerous parameters. The temporal dimension includes parameters such as dose rate and number of fractions, while spatial fractionation involves parameters such as field beamlet size and subunit intensity distribution. The values of these parameters will affect the plan quality. To achieve the best plan quality, it is often necessary to determine these parameter values using a reverse (i.e., automatic optimization) rather than a forward (i.e., manual trial and error) approach.

In this embodiment, combined with the expected clinical goals of clinical target coverage and organ-at-risk protection, the general form of the plan optimization model is described as follows:

$$\text{Minimize} f(B) =$$
$$w_{T,1}\sum_{i\epsilon T}\left(B_T^{min} - B_i\right)_+^2 + w_{T,2}\sum_{i\epsilon T}\left(B_i - B_T^{min}\right)_+^2 + w_{O,1}\sum_{i\epsilon O}(B_i - B_i^{max})_+^2 + w_{O,2}\sum_{i\epsilon 0}(B_i - B_i^{mean})_+^2 + w_{O,3}\sum_{i\epsilon 0}B_i - w_{T,3}\sum_{i\epsilon T}B_i$$

The constraints are:

$$B_i \le B_O^{max}\ \forall\ i\epsilon O$$
$$B_i \le B_T^{max}\ \forall\ i\epsilon T$$
$$B_i = \sum_{k=1}^{n} B_{ki}\ \forall\ i$$
$$B_{ki} = D_{ki} + \frac{1}{(a/\beta)_i}D_{ki}^2\ \forall\ i, \forall\ k$$
$$D_{ki} = \sum_j M_{kij}d_{ij}x_{kj}\ \forall\ i, \forall\ k$$
$$x_{kj} \ge 0\ \forall\ j, \forall\ k$$

Where, the objective function $f(B)$ represents the expected clinical goals of target coverage and organ-at-risk protection; the first term of the objective function represents the positive contribution of the minimum BED value ratio $B_i$ in the low-dose region of the target, the second term represents the positive contribution of the maximum BED value ratio Bain the high-dose region of the target, the third and fourth terms represent the positive contributions of the maximum and average BED values ratio $B_i$ in the organ-at-risk regions, the fifth and sixth terms represent the average BED value of normal tissue and the average BED value of the target; T represents the set of voxels contained in the target, O represents the set of all organ-at-risk tissue voxels, $w_T$ represents the relative importance weight for the target goal, $w_B$ represents the relative importance weight for the normal tissue goal, $$B_T^{min}$$

represents the minimum BED value of the target, $$B_O^{max}$$

represents the maximum BED value of normal tissue, $$B_i^{mean}$$

represents the average BED value of the respective tissue, $$B_i^{max}$$

represents the maximum BED value of the respective tissue, $D_{ki}$ is the physical dose of the voxel i in the kth fraction, $d_{ij}$ the dose-deposition matrix represents the dose contribution of the beam j per unit flux to the voxel i, $x_{kj}$ represents the flux weight of the beam j in the kth fraction, $B_i$ is the BED value of voxel i, $M_{kij}$ is the dose modification factor of beam j in voxel i in the kth fraction.

Figure 3:
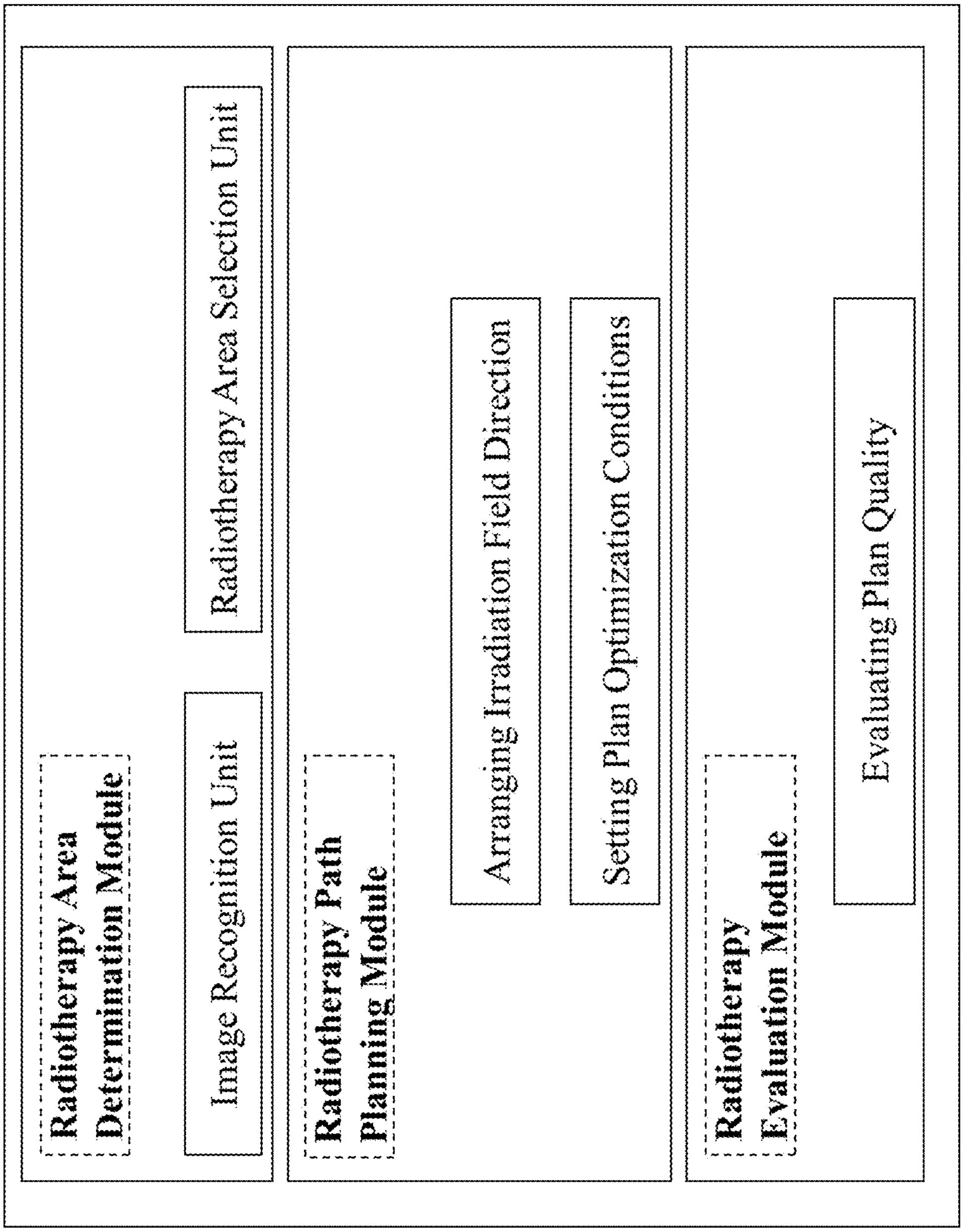
FIG. 3 is a functional block diagram of the system for determining the temporospatially-fractionated radiotherapy planning according to an embodiment of the present invention.

As shown in FIG. 3, based on the theoretical methods, this embodiment provides a temporospatially-fractionated radiotherapy system. The temporospatially-fractionated radiotherapy system is a tool for designing temporospatially-fractionated radiotherapy planning, mainly divided into the following 5 steps:

1. Input images and define the region of interest;
2. Arrange appropriate irradiation field directions according to the shape of the target area;
3. Set various plan optimization conditions according to clinical prescription requirements;
4. Evaluate the plan quality, re-optimize conditions for unsuitable plans until the plan quality meets the requirements;
5. Output the radiotherapy planning.

The dose modification factor models under different conditions are as follows:

(1) Temporally Fractionated Effect Model

Temporally fractionated radiotherapy refers to controlling the duration of irradiation by adjusting the radiation dose rate. Ultra-high dose rate radiotherapy has a better protective effect on normal tissues compared to conventional low dose rate radiotherapy. This effect is known as the ultra-high dose rate effect, which is a specific manifestation of the time fractionation effect under ultra-high dose rate conditions. The biological mechanism of the ultra-high dose rate effect is speculated to be related to the regulation of inflammatory cytokines and the different immune responses of tumor/normal tissues.

In this embodiment, the dose modification factor is used as a function to simulate the ultra-high dose rate effect, while also considering the dose and dose rate constraints induced by the ultra-high dose rate effect. The ultra-high dose rate effect and physical dose distribution are jointly optimized. From the results, this method quantifies the net change from conventional radiotherapy to ultra-high dose rate radiotherapy, more intuitively demonstrating the dosimetric advantages produced by the ultra-high dose rate effect.

Therefore, the calculation formula for the dose modification factor of the ultra-high dose rate effect $M^T$ is as follows:

$$M^T = \begin{cases} C, & \dot{D} \geq 40\ Gy/s \\ 1, & \dot{D} < 40\ Gy/s \end{cases}$$

$\dot{D}$ Represents the dose rate, greater than or equal to 40 Gy/s considering the ultra-high dose rate effect; less than 40 Gy/s not considering the ultra-high dose rate effect, it is considered that there is no normal tissue protection effect. C is a constant related to tissue characteristics, such as C≈0.7 for rat skin.

(2) Spatially Fractionated Effect Model

The spatially fractionated effect mainly considers the bystander effect, which plays a key role in cell survival under highly non-uniform radiation exposure. Although it has been speculated that the radiation-induced bystander effect involves multiple factors, there is no clear information about the actions of different molecules.

This embodiment acknowledges the potential impact of radiation-induced bystander effects on spatially fractionated radiotherapy, considering the hypothesis of equivalent range to be more applicable.

Therefore, this embodiment proposes the calculation formula for the dose modification factor of the spatially fractionated effect $M^S$ as follows:

$$M^S = \begin{cases} \dfrac{(2\beta D_{x\text{-}rays})}{\left(-\alpha + \sqrt{\alpha^2 - 4\beta \ln\left(P_0 + (1-P_0)e^{-k\tau}\right)}\right)}, & 0 \leq R \leq 20\text{ mm} \\ 1, & R > 20\text{ mm} \end{cases}$$

α and β are cell-specific parameters, $D_{x\text{-}rays}$ representing the physical absorbed dose corresponding to 10% cell survival fraction for tumor cells irradiated by X-rays. For abdominal sarcoma, $\alpha=0.253\text{Gy}^{-1}$ $\delta=0.0503\text{Gy}^{-2}$, $D_{x\text{-}rays}=4.72\text{Gy}$. $P_0$ representing the probability of cell survival after responding to the signal, with values obtained through cell experiments $P_0=0.6\pm0.4$ and k is the response coefficient, such as k=−0.002 for glioblastoma.

(3) Temporospatially-Fractionated Synergy Model

For temporospatially-fractionated radiotherapy, in addition to considering the effects of temporally fractionated and spatially fractionated radiotherapy, the synergistic effects of both should also be considered.

Therefore, this embodiment proposes the calculation formula for the dose modification factor of the temporospatially-fractionated effect $M^{TSF}$ as follows:

$$M^{TSF} = M^T \times M^S \times M^{TSS}$$

where $M^{TSF}$ is the dose modification factor of the spatiotemporal fractionation effect, $M^T$ is the dose modification factor of the temporally fractionated effect, $M^S$ is the dose modification factor of the spatially fractionated effect, and $M^{TSS}$ is the dose modification factor of the synergistic effect.

(4) Conventional Radiotherapy Model

For conventional radiotherapy, the dose modification factor is assumed to be 1 by default.

The linear-quadratic model under different conditions is as follows:

(1) If the dose of all fractions in a course of treatment is the same, the linear-quadratic model is $$B_i = n\left(M_{ki}D_{ki} + \frac{1}{(\alpha/\beta)_i}(M_{ki}D_{ki})^2\right)$$

$M_{ki}$ represents the dose modification factor for the biological effect at the kth fraction for voxel i.

(2) If the dose of all fractions in a course of treatment is different, the linear-quadratic model is $$B_i = \sum_{k=1}^{n}\left[M_{ki}D_{ki} + \frac{1}{(\alpha/\beta)_i}(M_{ki}D_{ki})^2\right]$$

$M_{ki}$ represents the dose modification factor for the biological effect at the kth fraction for voxel i.

(3) The LQ model for the temporally fractionated effect is:

If the dose of all fractions in a course of treatment is the same, the LQ model is $$B_i = n\left(M_{ki}^T D_{ki} + \frac{1}{(\alpha/\beta)_i}\left(M_{ki}^T D_{ki}\right)^2\right)$$

If the dose of all fractions in a course of treatment is different, the LQ model is $$B_i = \sum_{k=1}^{n}\left[M_{ki}^T D_{ki} + \frac{1}{(\alpha/\beta)_i}\left(M_{ki}^T D_{ki}\right)^2\right]$$

$$M_{ki}^T$$

represents the dose modification factor of voxel i at the kth fraction for the temporally fractionated effect.

(4) The LQ model for the spatially fractionated effect is:

If the dose of all fractions in a course of treatment is the same, the LQ model is $$B_i = n\left(M_{ki}^S D_{ki} + \frac{1}{(\alpha/\beta)_i}\left(M_{ki}^S D_{ki}\right)^2\right)$$

If the dose of all fractions in a course of treatment is different, the LQ model is $$B_i = \sum_{k=1}^{n}\left[M_{ki}^S D_{ki} + \frac{1}{(\alpha/\beta)_i}\left(M_{ki}^S D_{ki}\right)^2\right]$$

$$M_{ki}^S$$

represents the dose modification factor of voxel i at the kth fraction for the spatially fractionated effect.

(5) The LQ model for the temporospatially-fractionated effect is:

If the dose of all fractions in a course of treatment is the same, the linear-quadratic model is $$B_i = n\left(M_{ki}^{TSF} D_{ki} + \frac{1}{(\alpha/\beta)_i}\left(M_{ki}^{TSF} D_{ki}\right)^2\right)$$

If the dose of all fractions in a course of treatment is different, the linear-quadratic model is $$B_i = \sum_{k=1}^{n}\left[M_{ki}^{TSF} D_{ki} + \frac{1}{(\alpha/\beta)_i}\left(M_{ki}^{TSF} D_{ki}\right)^2\right]$$

$$M_{ki}^{TSF}$$

represents the dose modification factor of voxel i at the kth fraction for the temporospatially-fractionated effect.

The plan optimization model under different conditions is:

(1) Assuming Each Fractionated Plan is Different

The general optimization model becomes the following form:

Objective Function Minimize $$f(B) = w_{T,1}\sum_{i\epsilon T}\left(B_T^{min} - B_i\right)_+^2 + w_{O,1}\sum_{i\epsilon O}(B_i - B_i^{max})_+^2 + w_{O,2}\sum_{i\epsilon O}(B_i - B_i^{mean})_+^2 w_{O,3}\sum_{i\epsilon O} B_i - w_{T,2}\sum_{i\epsilon T} B_i$$

Constraints $$B_i \le B_O^{max} \quad \forall\, i \epsilon O$$

$$B_i \le B_T^{max} \quad \forall\, i \epsilon T$$

$$B_i = \sum_{k=1}^{n} B_{ki} \quad \forall\, i$$

$$B_{ki} = D_{ki} + \frac{1}{(\alpha/\beta)_i} D_{ki}^2 \quad \forall\, i, \forall\, k$$

$$D_{ki} = \sum_j M_{kji}^{TSF} d_{ij} x_{kj} \quad \forall\, i, \forall\, k \qquad 1$$

$$M_{kji}^{TSF} = M_{kji}^{T} + M_{kji}^{S} \quad \forall\, i, \forall\, k \qquad 2$$

$$M_{kji}^{T} = \begin{cases} C, & \dot{D}_u \ge 40\ Gy/s \\ 1, & \dot{D}_u < 40\ Gy/s \end{cases} \qquad 3$$

$$M_{kji}^{S} = \begin{cases} \dfrac{2\beta D_{x\text{-}rays}}{-\alpha + \sqrt{\alpha^2 - 4\beta \ln\left(P_0 + (1 - P_0)e^{-k\tau}\right)}}, & 0 \le R \le 20\ \text{mm} \\ 1, & R > 20\ \text{mm} \end{cases} \qquad 4$$

$$x_{kj} \ge 0 \quad \forall\, j, \forall\, k$$

$$M_{kji}^{TSF}$$

represents the dose modification factor of the beam j voxel i at the kth fraction for the temporospatially-fractionated effect.

(2) Assuming Each Fractionated Plan is the Same

When each plan is the same, i.e. $B_{ki}$, the BED value is the same under each fraction, the general optimization model simplifies to the following form:

Objective Function Minimize $$f(B) = w_{T,1}\sum_{i\epsilon T}\left(B_T^{min} - B_i\right)_+^2 + w_{O,1}\sum_{i\epsilon O}(B_i - B_i^{max})_+^2 + w_{O,2}\sum_{i\epsilon O}(B_i - B_i^{mean})_+^2 w_{O,3}\sum_{i\epsilon O} B_i - w_{T,2}\sum_{i\epsilon T} B_i$$

-continued

Constraints $$B_i \le B_O^{max} \quad \forall\, i \in O$$

$$B_i \le B_T^{max} \quad \forall\, i \in T$$

$$B_i = nD_i + \frac{nD_i^2}{(\alpha/\beta)_i} \quad \forall\, i$$

$$D_i = \sum\nolimits_j M_{ji}^{TST} d_{ij} x_j \quad \forall\, i$$

$$M_{kji}^{TSF} = M_{kji}^{T} + M_{kji}^{S} \quad \forall\, i$$

$$M_{ji}^{T} = \begin{cases} 0.7, & \dot{D}_u \ge 40\ Gy/s \\ 1, & \dot{D}_u < 40\ Gy/s \end{cases}$$

$$M_{ji}^{S} = \begin{cases} \dfrac{2\beta D_{x-rays}}{-\alpha + \sqrt{\alpha^2 - 4\beta \ln\left(P_0 + (1 - P_0)e^{-k\tau}\right)}}, & 0 \le R \le 20\text{ mm} \\ 1, & R > 20\text{ mm} \end{cases}$$

$$x_j \ge 0 \quad \forall\, j$$

$$M_{ji}^{TSF}$$

represents the dose modification factor of the beam j voxel i for the temporospatially-fractionated effect.

(3) Optimization Model for the Temporally Fractionated Effect (a) Assuming Each Fractionated Plan is Different The general optimization model becomes the following form:

Objective Function Minimize $$f(B) = w_{T,1}\sum\nolimits_{i\epsilon T}\left(B_T^{min} - B_i\right)_+^2 + w_{O,1}\sum\nolimits_{i\epsilon O}\left(B_i - B_i^{max}\right)_+^2 + w_{O,2}\sum\nolimits_{i\epsilon O}\left(B_i - B_i^{mean}\right)_+^2 w_{O,3}\sum\nolimits_{i\epsilon O}B_i - w_{T,2}\sum\nolimits_{i\epsilon T}B_i$$

Constraints $$B_i \le B_O^{max} \quad \forall\, i \in O$$

$$B_i \le B_T^{max} \quad \forall\, i \in T$$

$$B_i = \sum_{k=1}^{n} B_{ki} \quad \forall\, i$$

$$B_{ki} = D_{ki} + \frac{1}{(\alpha/\beta)_i} D_{ki}^2 \quad \forall\, i, \forall\, k$$

$$D_{ki} = \sum\nolimits_j M_{kji}^{T} d_{ij} x_{kj} \quad \forall\, i, \forall\, k$$

$$M_{kji}^{T} = \begin{cases} C, & \dot{D}_u \ge 40\ Gy/s \\ 1, & \dot{D}_u < 40\ Gy/s \end{cases}$$

$$x_{kj} \ge 0 \quad \forall\, j, \forall\, k$$

$$M_{kji}^{T}$$

represents the dose modification factor of the beam j voxel i at the kth fraction for the temporally fractionated effect.

(b) Assuming Each Plan is the Same

When each plan is the same, i.e. $B_{ki}$, the BED value is the same under each fraction, the general optimization model simplifies to the following form:

Objective Function Minimize $$f(B) = w_{T,1}\sum\nolimits_{i\epsilon T}\left(B_T^{min} - B_i\right)_+^2 + w_{O,1}\sum\nolimits_{i\epsilon O}\left(B_i - B_i^{max}\right)_+^2 +$$

-continued $$w_{O,2}\sum\nolimits_{i\epsilon O}(B_i - B_i^{mean})_+^2 w_{O,3}\sum\nolimits_{i\epsilon O}B_i - w_{T,2}\sum\nolimits_{i\epsilon T}B_i$$

Constraints $$B_i \le B_O^{max} \quad \forall\, i \epsilon O$$

$$B_i \le B_T^{max} \quad \forall\, i \epsilon T$$

$$B_i = nD_i + \frac{nD_i^2}{(\alpha/\beta)_i} \quad \forall\, i$$

$$D_i = \sum\nolimits_j M_{ji}^T d_{ij} x_j \quad \forall\, i$$

$$M_{ji}^T = \begin{cases} 0.7, & \dot{D}_u \ge 40\ Gy/s \\ 1, & \dot{D}_u < 40\ Gy/s \end{cases}$$

$$x_j \ge 0 \quad \forall\, j$$

$M_{ji}^T$ represents the dose modification factor of the beam j voxel i during the temporally fractionated effect.

(4) Plan Optimization Model for Spatially Fractionated Effect (a) Assuming Each Fractionated Plan is Different The general optimization model becomes the following form:

Objective Function Minimize $$f(B) = w_{T,1}\sum\nolimits_{i\epsilon T}(B_T^{min} - B_i)_+^2 + w_{O,1}\sum\nolimits_{i\epsilon O}(B_i - B_i^{max})_+^2 + w_{O,2}\sum\nolimits_{i\epsilon O}(B_i - B_i^{mean})_+^2 w_{O,3}\sum\nolimits_{i\epsilon O}B_i - w_{T,2}\sum\nolimits_{i\epsilon T}B_i$$

Constraints $$B_i \le B_O^{max} \quad \forall\, i \epsilon O$$

$$B_i \le B_T^{max} \quad \forall\, i \epsilon T$$

$$B_i = \sum_{k=1}^{n} B_{ki} \quad \forall\, i$$

$$B_{ki} = D_{ki} + \frac{1}{(\alpha/\beta)_i} D_{ki}^2 \quad \forall\, i, \forall\, k$$

$$D_{ki} = \sum\nolimits_j M_{kji}^S d_{ij} x_{kj} \quad \forall\, i, \forall\, k$$

$$M_{kji}^S = \begin{cases} \dfrac{2\beta D_{x-rays}}{-\alpha + \sqrt{\alpha^2 - 4\beta \ln\left(P_0 + (1-P_0)e^{-k\tau}\right)}}, & 0 \le R \le 20\ \text{mm} \\ 1, & R > 20\ \text{mm} \end{cases}$$

$$x_{kj} \ge 0 \quad \forall\, j, \forall\, k$$

$M_{kji}^S$ represents the dose modification factor of the beam j voxel i during the kth fraction of the spatially fractionated effect.

(2) Assuming Each Fractionated Plan is the Same

When each plan is the same, i.e. $B_{ki}$, the BED value is the same under each fraction, the general optimization model simplifies to the following form:

Objective Function Minimize $$f(B) = w_{T,1}\sum\nolimits_{i\epsilon T}(B_T^{min} - B_i)_+^2 + w_{O,1}\sum\nolimits_{i\epsilon O}(B_i - B_i^{max})_+^2 +$$

-continued $$w_{O,2}\sum_{i\epsilon O}(B_i - B_i^{mean})_+^2 w_{O,3}\sum_{i\epsilon O}B_i - w_{T,2}\sum_{i\epsilon T}B_i$$

Constraints $$B_i \le B_O^{max} \quad \forall\, i \epsilon O$$

$$B_i \le B_T^{max} \quad \forall\, i \epsilon T$$

$$B_i = nD_i + \frac{nD_i^2}{(\alpha/\beta)_i} \quad \forall\, i$$

$$D_i = \sum_j M_{ji}^S d_{ij} x_j \quad \forall\, i$$

$$M_{ji}^S = \begin{cases} \dfrac{2\beta D_{x-rays}}{-\alpha + \sqrt{\alpha^2 - 4\beta \ln\left(P_0 + (1-P_0)e^{-k\tau}\right)}}, & 0 \le R \le 20 \text{ mm} \\ 1, & R > 20 \text{ mm} \end{cases}$$

$$x_j \ge 0 \quad \forall\, j$$

$M_{ji}^{SF}$ represents the dose modification factor of the beam j voxel i during the spatial fractionation effect.

(5) Plan Optimization Model for TemporoSpatially-Fractionated Effect (a) Assuming Each Fractionated Plan is Different The general optimization model becomes the following form:

Objective Function Minimize $$f(B) = w_{T,1}\sum_{i\epsilon T}\left(B_T^{min} - B_i\right)_+^2 + w_{O,1}\sum_{i\epsilon O}(B_i - B_i^{max})_+^2 + w_{O,2}\sum_{i\epsilon O}(B_i - B_i^{mean})_+^2 w_{O,3}\sum_{i\epsilon O}B_i - w_{T,2}\sum_{i\epsilon T}B_i$$

Constraints $$B_i \le B_O^{max} \quad \forall\, i \epsilon O$$

$$B_i \le B_T^{max} \quad \forall\, i \epsilon T$$

$$B_i = \sum_{k=1}^{n} B_{ki} \quad \forall\, i$$

$$B_{ki} = D_{ki} + \frac{1}{(\alpha/\beta)_i} D_{ki}^2 \quad \forall\, i, \forall\, k$$

$$D_{ki} = \sum_j M_{kji}^{TSF} d_{ij} x_{kj} \quad \forall\, i, \forall\, k$$

$$M_{kji}^{TSF} = M_{kji}^T \times M_{kji}^S \times M_{kji}^{TSS} \quad \forall\, i, \forall\, k$$

$$M_{kji}^T = \begin{cases} C, & \dot{D}_u \ge 40\ Gy/s \\ 1, & \dot{D}_u < 40\ Gy/s \end{cases}$$

$$M_{kji}^S = \begin{cases} \dfrac{2\beta D_{x-rays}}{-\alpha + \sqrt{\alpha^2 - 4\beta \ln\left(P_0 + (1-P_0)e^{-k\tau}\right)}}, & 0 \le R \le 20 \text{ mm} \\ 1, & R > 20 \text{ mm} \end{cases}$$

$$x_{kj} \ge 0 \quad \forall\, j, \forall\, k$$

$M_{kji}^{TSF}$ represents the dose modification factor of the beam j voxel i at the kth fraction for the temporospatially-fractionated effect.

(b) Assuming Each Fractionated Plan is the Same

When each plan is the same, i.e. $B_{ki}$, the BED value is the same under each fraction, the general optimization model simplifies to the following form:

Objective Function: Minimize $$f(B) = w_{T,1}\sum_{i \epsilon T}\left(B_T^{min} - B_i\right)_+^2 + w_{O,1}\sum_{i \epsilon O}(B_i - B_i^{max})_+^2 + w_{O,2}\sum_{i \epsilon O}(B_i - B_i^{mean})_+^2 w_{O,3}\sum_{i \epsilon O}B_i - w_{T,2}\sum_{i \epsilon T}B_i$$

Constraints:

$$B_i \le B_O^{max} \quad \forall\, i \epsilon O$$

$$B_i \le B_T^{max} \quad \forall\, i \epsilon T$$

$$B_i = nD_i + \frac{nD_i^2}{(\alpha/\beta)_i} \quad \forall\, i$$

$$D_i = \sum_j M_{ji}^{TST} d_{ij} x_j \quad \forall\, i$$

$$M_{ji}^{TSF} = M_{ji}^T \times M_{ji}^S \times M_{ji}^{TSS} \quad \forall\, i$$

$$M_{ji}^T = \begin{cases} C, & \dot{D}_{tt} \ge 40\ Gy/s \\ 1, & \dot{D}_{tt} < 40\ Gy/s \end{cases}$$

$$M_{ji}^S = \begin{cases} \dfrac{2\beta D_{x-rays}}{-\alpha + \sqrt{\alpha^2 - 4\beta\ln\left(P_0 + (1 - P_0)e^{-k\tau}\right)}}, & 0 \le R \le 20\ \text{mm} \\ 1, & R > 20\ \text{mm} \end{cases}$$

$$x_j \ge 0 \quad \forall\, j$$

$$M_{ji}^{TSF}$$

represents the dose modification factor of the beam j voxel i during the temporospatially-fractionated effect.

Example 3

This Embodiment 3 provides a non-transitory computer-readable storage medium, which is used to store computer instructions. When the computer instructions are executed by a processor, they implement the method for determining a temporospatially-fractionated radiotherapy planning as described above. The method includes:

- Obtaining pathological images;
- Identifying the obtained pathological images to determine the region of interest in the pathological images as the radiotherapy region;
- Arranging the irradiation field direction according to the shape of the radiotherapy region, setting the optimization conditions of the radiotherapy planning according to clinical prescription requirements, and planning the radiotherapy path;
- For the planned radiotherapy path, evaluate the plan quality based on the plan optimization model, and reset the optimization conditions for unsuitable radiotherapy plans until the plan quality meets the requirements;
- Output the radiotherapy path that meets the plan quality requirements as the final temporospatially-fractionated radiotherapy planning.

Example 4

This Example 4 provides a computer program product, including a computer program, which, when run on one or more processors, is used to implement the method for determining a temporospatially-fractionated radiotherapy planning as described above. The method includes:

- Obtaining pathological images;
- Identifying the obtained pathological images to determine the region of interest in the pathological images as the radiotherapy region;
- Arranging the irradiation field direction according to the shape of the radiotherapy region, setting the optimization conditions of the radiotherapy planning according to clinical prescription requirements, and planning the radiotherapy path;
- For the planned radiotherapy path, evaluate the plan quality based on the plan optimization model, and reset the optimization conditions for unsuitable radiotherapy plans until the plan quality meets the requirements;
- Output the radiotherapy path that meets the plan quality requirements as the final temporospatially-fractionated radiotherapy planning.

Example 5

This Example 5 provides an electronic device, including: a processor, a memory, and a computer program; wherein the processor is connected to the memory, the computer program is stored in the memory, and when the electronic device is running, the processor executes the computer program stored in the memory to cause the electronic device to execute instructions to implement the method for determining a temporospatially-fractionated radiotherapy planning as described above. The method includes:

- Obtaining pathological images;
- Identifying the obtained pathological images to determine the region of interest in the pathological images as the radiotherapy region;

Arranging the irradiation field direction according to the shape of the radiotherapy region, setting the optimization conditions of the radiotherapy planning according to clinical prescription requirements, and planning the radiotherapy path;

For the planned radiotherapy path, evaluate the plan quality based on the plan optimization model, and reset the optimization conditions for unsuitable radiotherapy plans until the plan quality meets the requirements;

Output the radiotherapy path that meets the plan quality requirements as the final temporospatially-fractionated radiotherapy planning.

In summary, the embodiment of the invention proposes a new X-ray temporospatially-fractionated radiotherapy method, providing technical conditions for exploring various dose temporospatially-fractionated methods. The dose temporospatially-fractionated methods not only include current research hotspots (ultra-high dose rate radiotherapy and spatially fractionated radiotherapy) but also include areas in the temporospatial domain that have never been explored. The provided technical conditions can simulate the conditions of current clinical treatment for patients, such as multiple irradiation directions, field intensity adjustment, and precise positioning, and can also simulate conditions that may be used for patient treatment in the future, such as (ultra) high dose rates, small beam/microbeam, and temporospatial synchronous fractionation. The temporospatially-fractionated method proposed by the invention can unify various existing and unexplored dose fractionation methods, and its role and status in the field of radiotherapy are somewhat similar to the role and status of the unified field theory in the field of theoretical physics.

It should be understood by those skilled in the art that embodiments of the invention can be provided as a method, system, or computer program product. Therefore, the invention can take the form of an entirely hardware embodiment, an entirely software embodiment, or an embodiment combining software and hardware aspects. Moreover, the present invention can take the form of a computer program product embodied in one or more computer-readable storage media containing computer-readable program code (including but not limited to disk storage, CD-ROM, optical storage, etc.).

The invention is described with reference to flowcharts and/or block diagrams of methods, apparatus (systems), and computer program products according to embodiments of the invention. Each flow and/or block in the flowcharts and/or block diagrams, as well as combinations of flows and/or blocks in the flowcharts and/or block diagrams, can be implemented by computer program instructions. These computer program instructions can be provided to a general-purpose computer, special-purpose computer, embedded processor, or other programmable data processing apparatus to produce a machine, such that the instructions executed by the processor of the computer or other programmable data processing apparatus create means for implementing the functions specified in the flow or multiple flows and/or block or multiple blocks in the flowcharts and/or block diagrams.

These computer program instructions may also be stored in a computer-readable storage medium that can direct a computer or other programmable data processing apparatus to operate in a specific manner, such that the instructions stored in the computer-readable storage medium produce an article of manufacture that includes instruction means, which implement the functions specified in one or more flowcharts and/or one or more blocks of a block diagram.

These computer program instructions may also be loaded onto a computer or other programmable data processing apparatus to cause a series of operational steps to be performed on the computer or other programmable apparatus to produce a computer-implemented process, such that the instructions executed on the computer or other programmable apparatus provide steps for implementing the functions specified in one or more flowcharts and/or one or more blocks of a block diagram.

Although the above description of the specific embodiments of the invention has been made in conjunction with the accompanying drawings, it is not intended to limit the scope of protection of the invention. Those skilled in the art should understand that various modifications or variations can be made based on the technical solutions disclosed in the invention without creative labor, and should be covered within the scope of protection of the invention.

What is claimed is:

1. A method for determining a temporospatially-fractionated radiotherapy planning, comprising a computer readable medium operable on a computer with memory for the method for determining the temporospatially-fractionated radiotherapy planning, and comprising program instructions for executing the following steps of:

i) obtaining pathological images;

ii) identifying the obtained pathological images to determine region of interest in the pathological images as radiotherapy region;

iii) arranging irradiation field direction according to shape of the radiotherapy region, setting optimization conditions of the radiotherapy planning according to clinical prescription requirements, and planning radiotherapy path;

iv) for the planned radiotherapy path, evaluate plan quality based on a plan optimization model, and reset the optimization conditions for unsuitable radiotherapy plans until the plan quality meets requirements;

v) output the radiotherapy path that meets the plan quality requirements as final temporospatially-fractionated radiotherapy planning; and vi) performing multiple irradiation directions, field intensity adjustments, and precise positioning of radiotherapy device based on results of the method for determining the temporospatially-fractionated radiotherapy planning.

2. The method according to claim 1, wherein establishment of the plan optimization model comprises: establishing a dose modification factor model using the dose modification factor method; integrating the established dose modification factor model into the standard linear quadratic model to construct a new linear quadratic model; based on the linear quadratic model, combining the expected clinical goals of clinical target coverage and organ-at-risk protection to construct the plan optimization model.

3. The method according to claim 2, wherein the dose modification factor method is adopted, combining the temporally fractionated effect, the spatially fractionated effect, and the synergistic effect, to define a dose modification factor model, which is expressed by the formula:

$$M = M^T \times M^S \times M^{TSS};$$

where M represents the total dose modification factor; $M^T$ represents the biological effect of temporally fractionated radiotherapy; $M^S$ represents the biological effect of spatially fractionated radiotherapy; $M^{TSS}$ represents the synergistic effect between temporally and spatially fractionated effects.

4. The method according to claim 2, wherein constructing a linear quadratic model includes:

if the doses of all fractionated irradiations in a course are the same, the total biological effective dose for the course is:

$$B_i = nD_i\left(1 + \frac{D_i}{(\alpha/\beta)_i}\right)$$

where $B_i$ is the biological effective dose for voxel i, n is the number of irradiations, $D_i$ is the fractionated physical dose, and $(\alpha/\beta)_i$ is the biological characteristic dose of the tissue;

integrate the dose modification factor model M into the standard linear-quadratic model to obtain a new expression of the linear-quadratic model:

$$B_i = \sum_{k=1}^{n}\left[M_{ki}D_{ki} + \frac{1}{(\alpha/\beta)_i}(M_{ki}D_{ki})^2\right]$$

where, $M_{ki}$ represents the dose modification factor for the biological effect at the kth fraction for voxel i.

5. The method according to claim 2, characterized in that combining the expected clinical goals of clinical target coverage and organ-at-risk protection, the plan optimization model is as follows:

the objective function is:

$$\text{Minimize } f(B) = w_{T,1}\sum_{i\epsilon T}(B_T^{min} - B_i)_+^2 + w_{T,2}\sum_{i\epsilon T}(B_i - B_T^{min})_+^2 + w_{O,1}\sum_{i\epsilon O}(B_i - B_i^{max})_+^2 + w_{O,2}\sum_{i\epsilon O}(B_i - B_i^{mean})_+^2 + w_{O,3}\sum_{i\epsilon O}B_i - W_{T,3}\sum_{i\epsilon T}B_i$$

the constraints are:

$$\begin{aligned}
&B_i \le B_O^{max} && \forall\, i\epsilon O\\
&B_i \le B_T^{max} && \forall\, i\epsilon T\\
&B_i = \sum_{k=1}^{n} B_{ki} && \forall\, i\\
&B_{ki} = D_{ki} + \frac{1}{(\alpha/\beta)_i}D_{ki}^2 && \forall\, i, \forall\, k\\
&D_{ki} = \sum_j M_{kij}d_{ij}x_{kj} && \forall\, i, \forall\, k\\
&x_{kj} \ge 0 && \forall\, j, \forall\, k
\end{aligned}$$

where, the objective function $f(B)$ represents the expected clinical goals of target coverage and organ-at-risk protection; the first term of the objective function represents the positive contribution of the minimum BED value ratio $B_i$ in the low-dose region of the target, the second term represents the positive contribution of the maximum BED value ratio $B_i$ in the high-dose region of the target, the third and fourth terms represent the positive contributions of the maximum and average BED values ratio $B_i$ in the organ-at-risk regions, the fifth and sixth terms represent the average BED value of normal tissue and the average BED value of the target; T represents the set of voxels contained in the target, O represents the set of all organ-at-risk tissue voxels, $w_T$ represents the relative importance weight for the target goal, $w_B$ represents the relative importance weight for the normal tissue goal, $$B_T^{min}$$

represents the minimum BED value of the target, $$B_O^{max}$$

represents the maximum BED value of normal tissue, $$B_i^{mean}$$

represents the average BED value of the respective tissue, $$B_i^{max}$$

represents the maximum BED value of the respective tissue, $D_{ki}$ is the physical dose of the voxel i in the kth fraction, $d_{ij}$ the dose-deposition matrix represents the dose contribution of the beam j per unit flux to the voxel i, $x_{kj}$ represents the flux weight of the beam j in the kth fraction, $B_i$ is the BED value of voxel i, $M_{kij}$ is the dose modification factor of beam j in voxel i in the kth fraction.

6. The method according to claim 3, characterized in that the calculation formula for the dose modification factor of the ultra-high dose rate effect $M^T$ is as follows:

$$M^T = \begin{cases} C, & \dot{D} \ge 40\ Gy/s \\ 1, & \dot{D} < 40\ Gy/s \end{cases}$$

$\dot{D}$ represents the dose rate, which is greater than or equal to 40 Gy/s considering the ultra-high dose rate effect; less than 40 Gy/s that does not consider the ultra-high dose rate effect, C is a constant related to tissue characteristics;

the calculation formula for the dose modification factor of the spatially fractionated effect $M^S$ is as follows:

$$M^S = \begin{cases} \dfrac{2\beta D_{x\text{-}rays}}{-\alpha + \sqrt{\alpha^2 - 4\beta\ln\left(P_0 + (1 - P_0)e^{-k\tau}\right)}}, & 0 \le R \le 20\text{ mm} \\ 1, & R > 20\text{ mm} \end{cases}$$

α and β are cell-specific parameters, $D_{x\text{-}rays}$ representing the physical absorbed dose corresponding to 10% cell survival fraction in tumor cells irradiated by X-rays, $P_0$ representing the probability of cell survival after responding to the signal, and k is the response coefficient.

7. A system for determining a temporospatially-fractionated radiotherapy planning, comprising:

acquisition module, used for acquiring pathological images;

radiotherapy region determination module, used for identifying the acquired pathological images and determining the region of interest in the pathological images as the radiotherapy region;

radiotherapy path planning module, used for arranging the irradiation field direction according to the shape of the radiotherapy region, setting the optimization conditions of the radiotherapy plan according to clinical prescription requirements, and planning the radiotherapy path;

radiotherapy evaluation module, used for evaluating the quality of the planned radiotherapy path based on the plan optimization model, and resetting the optimization conditions for unsuitable radiotherapy plans until the plan quality meets the requirements; and output module, used to output the radiotherapy path that meets the plan quality requirements, as the final temporospatially-fractionated radiotherapy planning.

8. The system according to claim 7, wherein the radiotherapy area determination module includes an image recognition unit and a radiotherapy area selection unit, wherein the image recognition unit is used to identify the acquired pathological images, and the radiotherapy area selection unit is used to determine the region of interest in the pathological images as the radiotherapy area.

* * * * *